United States Patent [19]

Herbstman

[11] 4,316,724
[45] Feb. 23, 1982

[54] GASOLINE AND ALCOHOL BLENDS

[75] Inventor: Sheldon Herbstman, Spring Valley, N.Y.

[73] Assignee: Texaco Inc., White Plains, N.Y.

[21] Appl. No.: 146,841

[22] Filed: May 5, 1980

[51] Int. Cl.$^3$ .............................................. C10L 1/18
[52] U.S. Cl. ....................................................... 44/56
[58] Field of Search ..................... 44/56; 568/697, 895, 568/896

[56] References Cited

U.S. PATENT DOCUMENTS

| | | | |
|---|---|---|---|
| 3,822,119 | 9/1974 | Frech et al. | 44/56 |
| 4,071,567 | 1/1978 | Ancillotti et al. | 568/697 |
| 4,180,688 | 12/1979 | Imaizumi et al. | 568/895 |

Primary Examiner—Winston A. Douglas
Assistant Examiner—Y. Harris-Smith
Attorney, Agent, or Firm—Carl G. Ries; Robert A. Kulason; Carl G. Seutter

[57] ABSTRACT

Gasahol is made from aqueous alcohol, a portion of the water being removed by reaction with isobutene to form t-butyl alcohol.

9 Claims, 1 Drawing Figure

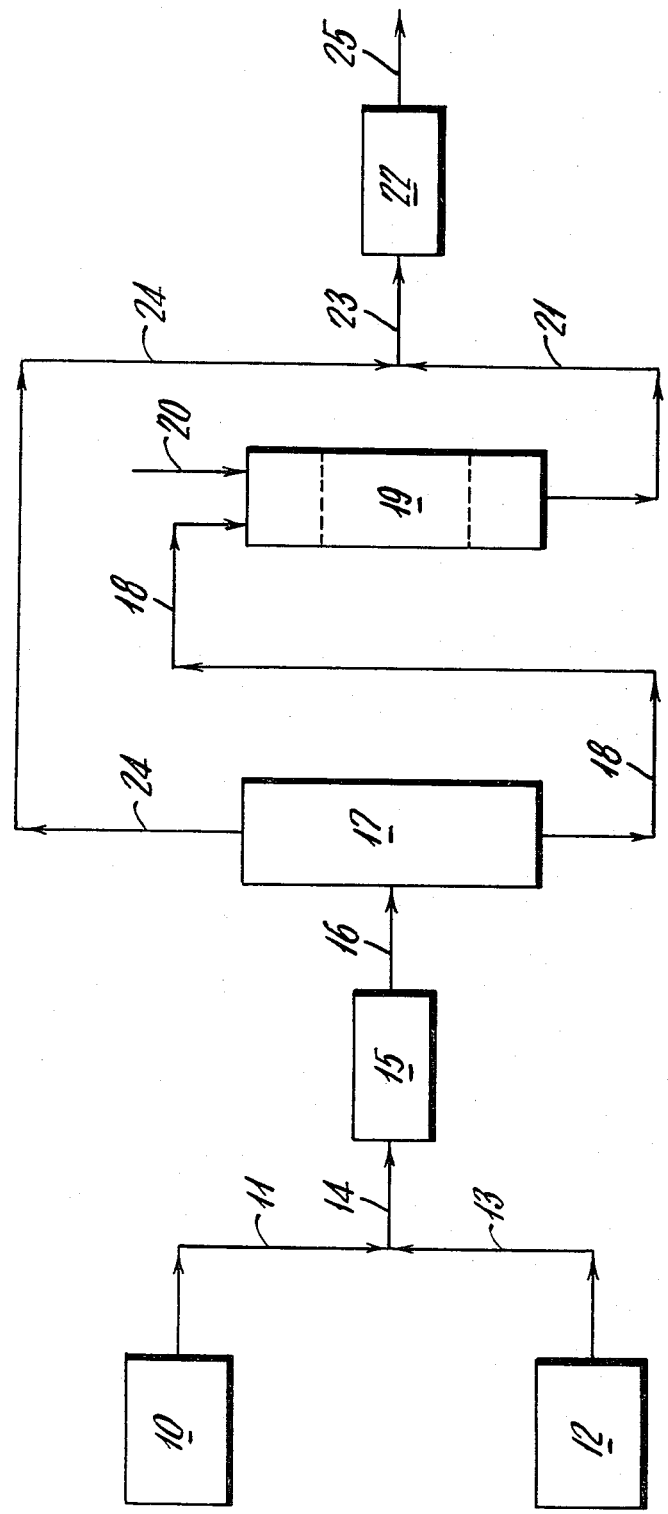

GASOLINE AND ALCOHOL BLENDS

FIELD OF THE INVENTION

This invention relates to a method of improving blends of gasoline and alcohol to increase the tolerance to water of the product.

BACKGROUND OF THE INVENTION

As is well known to those skilled in the art, gasoline may be extended by addition thereto of ethanol. It is found however that in order to prepare satisfactory one-phase composition, it is necessary to utilize absolute or anhydrous alcohol. Use of a dilute aqueous alcohol results in a two-phase system which is undesirable.

It is an object of this invention to provide a novel single phase gasoline composition and a method of forming the same from aqueous alcohols. Other objects will be apparent to those skilled in the art.

STATEMENT OF THE INVENTION

In accordance with certain of its aspects, the method of this invention may comprise
(i) mixing gasoline and aqueous ethanol thereby forming a two-phase system including an upper layer containing gasoline and ethanol and a lower layer containing water, ethanol, and gasoline;
(ii) contacting said lower layer with isoolefin, typically isobutylene or isoamylene, in the presence of etherification-alcoholification catalyst at etherification-alcoholification conditions including temperature of 100° F.–300° F. thereby converting the ethanol in said lower layer to ether and converting the water in said lower layer to tertiary alcohol thereby forming a converted lower layer containing ether and tertiary alcohol;
(iii) mixing said converted lower layer containing ether and tertiary alcohol with said upper layer containing gasoline and ethanol thereby forming a product gasoline composition containing gasoline, ethanol, ether, and tertiary alcohol; and
(iv) recovering said product gasoline composition containing gasoline, ethanol, ether, and tertiary alcohol.

DESCRIPTION OF THE INVENTION

The gasolines (including naphthas) which may be treated by the process of this invention may typically be motor fuels. It may for a naphtha be characterized by its ibp of 200° F. and its ep of 320° F. It may be a 100 octane blended gasoline having an ep of 320° F. It may be a lead-free gasoline having octane numbers of 92 (RON) and 82.4 (MON clear).

Although it may be possible to utilize, in practice of this invention, water-miscible alcohols such as n-propyl alcohol, isopropyl alcohol, hexylene glycol-2,3, it is a feature of the process of this invention that it finds greatest use in connection with ethanol. Alcohols, such as isobutanol, n-butanol, etc. which are only partially miscible with water and with hydrocarbon may be employed but their use is generally not advantageous.

It is a feature of the process of this invention that it is found to be particularly advantageous when used in connection with water-miscible alcohols—particularly ethanol. The alcohol may be employed in the form of aqueous systems containing water in amount of eg 1 v %–10 v %. It will be apparent that ease of operation is achieved with lesser quantities of water.

In practice of the process of this invention, the charge hydrocarbon fuel, preferably dry gasoline, is mixed with the ethanol which is miscible with the hydrocarbon fuel.

The liquid hydrocarbon charge may be mixed with 1 v %–25 v % or more, typically 5 v %–10 v %, say 10 v % of ethanol which is miscible with the hydrocarbon fuel. In one embodiment 90 volumes of gasoline may be mixed with 10 volumes of 95 w % ethanol. In another embodiment 80 volumes of gasoline may be mixed with 20 volumes of 95 w % ethanol.

Mixing may be effected by passing the two charge components into a vessel with or without agitation. Preferably it is effected by passing the two charge components through a packed bed of inert materials, this being effected at 25° F.–125° F., say ambient temperature of 75° F.

The uniformly mixed composition is found to be a two-phase mixture including an upper hydrocarbon layer and a lower aqueous layer. It is generally found that the upper hydrocarbon layer contains a major portion of the charge i.e. 90 v %–99 v %, say 98 v % while the lower aqueous layer contains a minor portion of the charge i.e. 1 v %–10 v %, say 2 v %. In the case of gasoline for example, 100 volumes of charge may typically give 98.5 parts of upper hydrocarbon layer containing 89 parts of gasoline, 9.2 parts of ethanol, and 0.3 parts of water and 1.5 parts of a lower aqueous layer containing 0.2 parts of water, 1.0 parts of ethanol, and 0.3 parts of gasoline.

The uniformly mixed two-phase composition is passed to a settling (or separation) operation wherein at 60° F.–125° F., say 75° F., the two phases separate after an effective residence time of 5–120 minutes, say about one hour.

The upper layer may contain 85–95 v % gasoline, say about 90 v %, 5–15 v %, say about 10 v % ethanol, and water in amount of about 0.5 v % or less, say 0.3 v %. The lower layer may contain ethanol in amount of 55–75 v %, say about 65 v %, gasoline in amount of 10–30 v %, say about 20 v %, and water in amount of 5–30 v % say about 14 v %.

The quantity and composition of lower layer recovered from separation will be a function of the amount of water in the charge gasoline and more particularly in the charge alcohol. If the alcohol be e.g. ethanol (containing say 95 w % ethanol as in the preferred embodiment), the lower layer may be 2–10 v %, say 5 v % of the total of the charge to separation.

The lower layer from separation is preferably separated and passed to a reaction operation together with isobutene, or a crude stream of C-4 olefins. Reaction is carried out at 100° F.–300° F., preferably 150° F.–250° F., say 200° F. and 50–750 psig, preferably 50–500 psig, say 300 psig. The ratio of isobutene to (water plus alcohol) may be 2-1, preferably 1.5-1, say 1:1.

Catalyst in the reaction zone is preferably a bed of granular solid resin etherification-alcoholification catalyst. These catalysts are preferably relatively high molecular weight carbonaceous material containing at least one-$SO_3H$ group as the functional group. Typical of these catalysts are the sulfonated coals ("Zeo-Karb H," "Nalcite X" and "Nalcite AX") produced by the treatment of bituminous coal with sulfuric acid. These materials are usually available in a neutralized form and in this case must be activated to the hydrogen form by treatment with a strong mineral acid such as hydrochloric acid, followed by water washing to remove sodium and chloride ions prior to use.

The sulfonated resin type catalysts are preferred for use in the present invention. These catalysts include the reaction products of phenolformaldehyde resins and sulfuric acid ("Amberlite IR-1", "Amberlite IR-100", and "Naleite MX"). Also useful are the sulfonated resinous polymers of coumarone-indene with cyclopentadiene, sulfonated polymers of coumarone-indene with furfural; sulfonated polymers of coumarone-indene with cyclopentadie and furfural; and sulfonated polymers of cyclopentadiene with furfural.

The most preferred cationic exchange resins are strongly acidic exchange resins consisting essentially of sulfonated polystyrene resin, for instance, a divinylbenze cross-linked polystyrene matrix having 0.5-20% are preferably 4-16% of copolymerized divinylbenzene therein bearing ionizable or functional nuclear sulfonic acid groups. These resins are manufactured and sold commercially under various trade names such as "Dowex 50", "Nalcite HCR" and "Amberlyst 15". As commercially obtained they have a solvent content of about 50% and can be used as is or the solvent can be removed first. The resin particle size may typically be 10 to 50 mesh (U.S. Sieve Series).

It is unexpectedly found that in the reaction operation, isoolefin reacts with the water present to form tertiary alcohol and with the ethanol present to form ether. If the isoolefin is isobutene and the alcohol is ethanol, then water and ethanol may be converted to t-butyl alcohol and ethyl-t-butyl ether respectively. If the isoolefin is isoamylene and the alcohol ethanol, for example, then the water and ethanol may be converted to t-amyl alcohol and ethyl-t-amyl alcohol.

The converted lower layer or bottom product contains 5-35 v %, preferably 10-30 v %, say about 20 v % gasoline, 40-80 v %, preferably 50-70 v %, say about 60 v % ether, and 10-40 v %, preferably 10-30 v %, say about 20 v % tertiary alcohol. In a typical instance, the bottom product contains 9.9 v % gasoline, 60.7 v % ethyl-t-butyl ether, and 29.4 v % t-butyl alcohol. This converted lower layer product is substantially free of ethyl alcohol and water—typically containing 1 v %-10 v %. usually less than 5 v % alcohol and 1 v %-10 v %, usually less than 5 v % water.

The converted lower layer is blended or mixed with the upper layer earlier recovered to form a product gasoline composition containing 80-97 volumes, say about 88 volumes of gasoline; 5-15 volumes, say about 9 volumes of ethanol; 1-5 volumes, say about 2 volumes of ether; and 0.5-5 volumes, say about 1 volume tertiary alcohol; and less than 0.5 volumes, typically 0.2-0.5 volumes, say about 0.3 volumes of water.

One illustrative product composition prepared from dry gasoline, 95 w % ethanol, and isobutylene may contain:
- 87.8 v %: gasoline
- 9.1 v %: ethanol
- 0.3 v %: water
- 1.85 v %: ethyl, t-butyl ether
- 0.9 v %: t-butyl alcohol The gasoline composition product is generally characterized by a satisfactory RVP and by an improved octane number. The RON may be increased by 1-5, say 3 over that of the charge; and the MON (clear) may also be improved by 1-4, say 2.

The single phase product is particularly characterized by an improved water tolerance over that of the charge gasoline. For example a typical charge gasoline will have a water tolerance of 0.1 ml while a typical product gasoline composition will have a water tolerance of about 0.5 ml. Water tolerance is the number of milliliters of water which can be added to 200 ml of a test gasoline at 75° F. before the gasoline-mixture acquires a noticeable haze.

DESCRIPTION OF THE BEST MODE

Practice of the process of this invention will be apparent to those skilled in the art from the following description of the best mode contemplated for carrying out the invention. As elsewhere in this specification, all parts are parts by weight unless otherwise specified. It will be apparent that the drawing is schematic and does not show details of processing equipment including pumps, heat exchangers, vessels, etc.

EXAMPLE I

In this example, there are charged 385 volumes of 95 w % ethanol from vessel 10 through line 11. There are also charged from vessel 12 through line 13, 3406 volumes of charge gasoline having octane numbers of 95.9 (RON) and 84.4 (MON Clear) and a water tolerance of 0.1. This lead-free gasoline had an IBP of 76° F., a 50% bp of 212° F. and an EP of 414° F.

These two streams are commingled in line 14 and passed to mixing operation 15 at ambient temperature of 75° F. The mixed system is withdrawn through line 16 and passed to settling operation 17. After an effective settling time of about one hour, there is formed a two-phase system including 3733 volumes of an upper layer containing gasoline (3371 volumes—90.3 v %) and ethanol (351 volumes—9.4 v %) together with water (11 volumes—0.3 v %) and 58 volumes of a lower layer containing 8.1 volumes (14.1 v %) water, 38.3 volumes (65.9 v %) ethanol, and 11.1 volumes (20.0 v %) gasoline.

The 58 volumes of lower layer, which is only about 1.5% of the total in settling operation 17 is withdrawn through line 18 and admitted to reaction operation 19. Also admitted through line 20 is 59 volumes (at STP) of isobutylene.

Reaction operation 19 includes a packed bed of 10-50 mesh Amberlyst 15 brand of hydrogen form of divinylbenzene cross-linked, sulfonated polystyrene solid resin catalyst. As the reactants pass downwardly through the bed at WHSV of 2-4, based on isobutene charge, the reactor is maintained at 100 psig and 210° F. During passage through the catalyst bed, the isobutene reacts with the ethanol to form ethyl, t-butyl ether; and the isobutene reacts with the water to form t-butyl alcohol.

The converted lower layer or bottom product contains 11.6 volumes (9.9 v %) gasoline, 71.1 volumes (60.7 v %) ethyl, t-butyl ether, and 34.5 volumes (29.4 v %) t-butyl alcohol; and it is substantially free of ethanol and water.

This product (117.2 volumes) is withdrawn through line 21 and passed via line 23 to product mixing operation 22. There is also admitted to line 23 and mixing operation 22, through line 24, 3733 volumes of upper layer from operation 17.

Product (3850 volumes) leaving mixing operation 22 through line 25 contains 3382 volumes (87.8 v %) gasoline, 351 volumes (9.1 v %) ethanol, 11 volumes (0.3 v %) water, 71.0 volumes (1.85 v %) ethyl, t-butyl ether, and 34.5 volumes (0.9 v %) t-butyl alcohol. This product has a higher RON (96.6) and MON (84.8) than the charge. Product RVP is 10.0 Water tolerance is 0.5. The IBP is 76° F., 50% point is 212° F., and EP is 414° F.

It will be noted that the product is particularly characterized by the following advantages:
(i) it contains about 9.1 v % ethanol;
(ii) although it was made from 95 w % ethanol, it is a single phase product containing only about 0.3 v % water;
(iii) a portion of the water present has been converted to t-butyl alcohol which is a more desirable component of a gasoline;
(iv) a portion of the ethanol present has been converted to ethyl, t-butyl ether which is a more desirable component of a gasoline;
(v) the RON has been increased from 95.9 to 96.6;
(vi) the MON has been increased from 84.4 to 84.8; and
(vii) the water tolerance of this product has been increased from 0.1 up to 0.5—a factor of 5.

Although this invention has been illustrated by reference to specific embodiments, it will be apparent to those skilled in the art that various changes and modifications may be made which clearly fall within the scope of this invention.

I claim:
1. The method which comprises
   (i) mixing gasoline and aqueous ethanol thereby forming a two-phase system including an upper layer containing gasoline and ethanol and a lower layer containing water, ethanol, and gasoline;
   (ii) contacting said lower layer with isobutylene or isoamylene olefin in the presence of etherification-alcoholification catalyst at etherification-alcoholification conditions including temperature of 100° F.–300° F. whereby the ethanol in said lower layer reacts with olefin to form ether and the water in said lower layer reacts with olefin to form tertiary alcohol thereby forming a lower layer containing ether and tertiary alcohol;
   (iii) mixing said lower layer containing ether and tertiary alcohol with said upper layer containing gasoline and ethanol thereby forming a product gasoline composition containing gasoline, ethanol, ether, and tertiary alcohol; and
   (iv) recovering said product gasoline composition containing gasoline, ethanol, ether, and tertiary alcohol.

2. The method claimed in claim 1 wherein said alcohol is ethanol containing 1 v %–10 v % water.
3. The method claimed in claim 1 wherein said alcohol is 95 w % ethanol.
4. The method claimed in claim 1 wherein said olefin is isobutylene.
5. The method which comprises
   (i) mixing gasoline and aqueous ethanol thereby forming a two-phase system including an upper layer containing gasoline and ethanol and a lower layer containing water, ethanol, and gasoline;
   (ii) separating said lower layer from said upper layer;
   (iii) contacting said lower layer with isobutylene in the presence of etherification-alcoholification catalyst at etherification-alcoholification conditions including temperature of 100° F.–300° F. whereby the ethanol in said lower layer reacts with isobutylene to form ethyl-t-butyl ether and the water in said lower layer reacts with isobutylene to form tertiary butyl alcohol thereby forming a lower layer containing ether and tertiary butyl alcohol;
   (iv) mixing said lower layer containing ethyl, t-butyl ether and tertiary butyl alcohol with said upper layer containing gasoline and ethanol thereby forming a product gasoline composition containing gasoline, ethanol, ethyl-t-butyl ether, and tertiary butyl alcohol; and
   (v) recovering said product gasoline composition containing gasoline, ethanol, ethyl-t-butyl ether, and tertiary butyl alcohol.

6. A composition comprising
a major portion of gasoline, and minor portions of ethanol; water; ethyl, tertiary C-3 alkyl or C-4 alkyl ether and tertiary C-3 alkyl or C-4 alkyl alcohol wherein the tertiary C-3 alkyl or C-4 alkyl groups of said ether and said alcohol are the same.

7. A composition comprising 80–97 volumes of gasoline; 5–15 volumes of ethanol; 1–5 volumes of ethyl, tertiary C-3 alkyl or C-4 alkyl ether; 0.5–5 volumes of tertiary C-3 alkyl or C-4 alkyl alcohol; and less than about 0.5 volumes of water.

8. A composition comprising 80–97 volumes of gasoline; 5–15 volumes of ethanol; 1–5 volumes of ethyl, t-butyl ether; 0.5–5 volumes of t-butyl alcohol; and less than about 0.5 volumes of water.

9. A composition comprising 80–97 volumes of gasoline; 5–15 volumes of ethanol; 1–5 volumes of ethyl, t-amyl ether; 0.5–5 volumes of t-amyl alcohol; and less than about 0.5 volumes of water.

* * * * *